(12) United States Patent
Suzuki (10) Patent No.: US 11,517,190 B2
(45) Date of Patent: Dec. 6, 2022

(54) ENDOSCOPE CONNECTING TUBE, LIQUID FEEDING APPARATUS, AND ENDOSCOPE REPROCESSING METHOD

(71) Applicant: OLYMPUS CORPORATION, Tokyo (JP)

(72) Inventor: Eiri Suzuki, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 579 days.

(21) Appl. No.: 16/666,512

(22) Filed: Oct. 29, 2019

(65) Prior Publication Data
US 2020/0060535 A1 Feb. 27, 2020

Related U.S. Application Data

(63) Continuation of application No. PCT/JP2018/006029, filed on Feb. 20, 2018.

(30) Foreign Application Priority Data

May 1, 2017 (JP) .............................. JP2017-091221

(51) Int. Cl.
*A61B 1/12* (2006.01)
*A61B 1/00* (2006.01)
(Continued)

(52) U.S. Cl.
CPC .......... *A61B 1/125* (2013.01); *A61B 1/00128* (2013.01); *A61B 90/70* (2016.02);
(Continued)

(58) Field of Classification Search
CPC ..... A61B 90/70; A61B 1/00128; A61B 1/125; A61B 2090/701; A61B 1/015; A61B 1/12; A61B 2090/0807; G02B 23/24
See application file for complete search history.

(56) References Cited

U.S. PATENT DOCUMENTS

2005/0196314 A1* 9/2005 Petersen ................ A61B 90/70
422/62
2006/0224042 A1* 10/2006 Jackson .................... A61L 2/18
600/133
(Continued)

FOREIGN PATENT DOCUMENTS

EP 3050493 A1 8/2016
JP 2002-263066 A 9/2002
(Continued)

OTHER PUBLICATIONS

International Search Report dated May 15, 2018 issued in PCT/JP2018/006029.

*Primary Examiner* — Benjamin L Osterhout
(74) *Attorney, Agent, or Firm* — Scully, Scott, Murphy & Presser, P.C.

(57) ABSTRACT

An endoscope connecting tube includes a liquid feeding index including: an exterior; an exposure hole provided on the exterior; and a flow path; and a movable member that is brought into a convex warp state toward a surface direction of the exterior when an inner pressure of a flow path reaches a predetermined value or higher, and remains in the convex warp state even when the inner pressure of the flow path reaches less than the predetermined value; and a marker that projects from the exposure hole by the movable member being brought into the convex warp state; a releasing portion that releases the convex warp state of the movable member by causing the marker to slide and push the movable member; and an insertion path into which the releasing portion is inserted.

20 Claims, 10 Drawing Sheets

(51) Int. Cl.
*A61B 90/70* (2016.01)
*A61B 90/00* (2016.01)
*G02B 23/24* (2006.01)

(52) U.S. Cl.
CPC ......... *A61B 1/12* (2013.01); *A61B 2090/0807* (2016.02); *A61B 2090/701* (2016.02); *G02B 23/24* (2013.01)

(56) References Cited

U.S. PATENT DOCUMENTS

2016/0236248 A1   8/2016   Iwasaki
2018/0071418 A1*  3/2018   Bommarito ............ A61B 1/122
2019/0175775 A1*  6/2019   Fryer ........................ A61L 2/28

FOREIGN PATENT DOCUMENTS

| JP | 2002-360515 A | 12/2002 |
| JP | 2008-178614 A | 8/2008 |
| JP | 2008-183296 A | 8/2008 |
| WO | WO 2016/009684 A1 | 1/2016 |

\* cited by examiner

ENDOSCOPE CONNECTING TUBE, LIQUID FEEDING APPARATUS, AND ENDOSCOPE REPROCESSING METHOD

CROSS REFERENCE TO RELATED APPLICATION

This application is a continuation application of PCT/JP2018/006029 filed on Feb. 20, 2018 and claims benefit of Japanese Application No. 2017-091221 filed in Japan on May 1, 2017, the entire contents of which are incorporated herein by this reference.

BACKGROUND OF THE INVENTION

1. Field of the Invention

The present invention relates to an endoscope connecting tube, a liquid feeding apparatus, and an endoscope reprocessing method.

2. Description of the Related Art

Conventionally, endoscopes have been used by being inserted into a subject, and thereafter connected to an endoscope reprocessor through an endoscope connecting tube and reprocessed for reuse. As a technique for endoscopes, a technique for indicating that the endoscopes have been reprocessed is proposed, in order to prevent the endoscopes which remain unprocessed from being reused. For example, Japanese Patent Application Laid-Open Publication No. 2002-360515 discloses the endoscope in which, after the cleaning of the endoscope by the endoscope cleaning apparatus, data indicating that the endoscope has been cleaned is received from the endoscope cleaning apparatus and the received data is displayed on the display device.

SUMMARY OF THE INVENTION

An endoscope connecting tube according to one aspect of the present invention includes: a tube; a first connector provided to a first end portion of the tube, and configured to be connected to an endoscope pipe sleeve; a second connector provided to a second end portion of the tube, and configured to be connected to a liquid feeding apparatus; a liquid feeding index arranged to at least one of the first connector and the second connector, the liquid feeding index comprising: an exterior; an exposure hole formed on the exterior; a flow path arranged in the exterior and communicated with the tube; a movable member arranged in the exterior, the movable member being brought into a convex warp state toward a surface direction of the exterior when an inner pressure of the flow path reaches a predetermined value or higher, the movable member remaining in the convex warp state even when the inner pressure of the flow path reaches less than the predetermined value; and a marker arranged so as to contact the movable member, the marker being configured to project from the exposure hole by the movable member being brought into the convex warp state; a releasing portion configured to release the convex warp state of the movable member by causing the marker to slide and push the movable member; and an insertion path into which the releasing portion is inserted, the insertion path being formed on the exterior.

A liquid feeding apparatus according to one aspect of the present invention includes: a fluid supplying apparatus; a connector communicating with the fluid supplying apparatus; and the above-described endoscope connecting tube.

An endoscope connecting tube according to another aspect of the present invention includes: a liquid feeding index including a marker that is reversibly switchable between a projected state and a non-projected state; and a tube. The marker is brought into the projected state when liquid flows in the tube and into the non-projected state when the marker is pushed.

An endoscope reprocessing method according to one aspect of the present invention is a method using an endoscope connecting tube including a marker that is reversibly switchable between a projected state and a non-projected state. The method includes connecting the endoscope connecting tube to an endoscope, with the marker brought into the non-projected state by the endoscope connecting tube being grasped.

DETAILED DESCRIPTION OF THE PREFERRED EMBODIMENTS

Hereinafter, embodiments of the present invention will be described with reference to drawings.

Configuration of Endoscope 1

Description will be made on a configuration of the endoscope 1.

Figure 1:
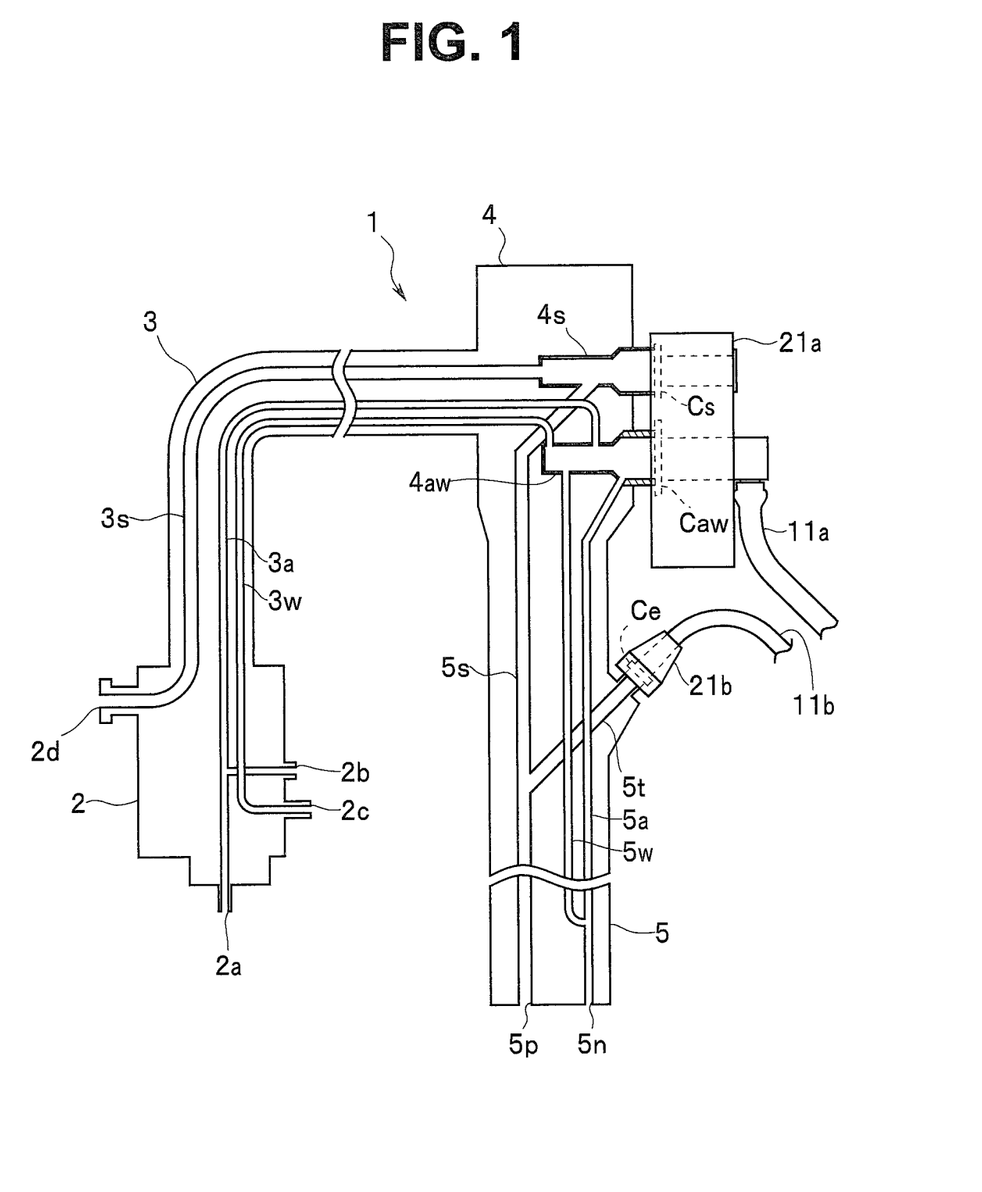
FIG. 1 is an illustration diagram of a configuration example of an endoscope and an endoscope connecting tube according to a first embodiment of the present invention.

FIG. 1 an illustration diagram of the configuration example of the endoscope 1 and endoscope connecting tubes 11a and 11b according to the first embodiment of the present invention.

As shown in FIG. 1, the endoscope 1 includes a scope connector 2, a universal cable 3 extending from the scope connector 2, an operation portion 4 connected with the universal cable 3, and an insertion portion 5 extending from the operation portion 4.

The scope connector 2 includes air-feeding pipe sleeves 2a, 2b, a water-feeding pipe sleeve 2c, and a suction pipe sleeve 2d.

Each of the air-feeding pipe sleeves 2a, 2b is communicated with an air/water feeding cylinder 4aw provided in the operation portion 4, through an air feeding pipe 3a. The air/water feeding cylinder 4aw is communicated with an air/water feeding nozzle 5n provided at the distal end portion of the insertion portion 5, through an air feeding pipe 5a.

The water feeding pipe sleeve 2c is also communicated with the air/water feeding cylinder 4aw through a water feeding pipe 3w. The air/water feeding cylinder 4aw is communicated also with the water feeding pipe 5w. In the insertion portion 5, the water feeding pipe 5w is connected with the air feeding pipe 5a to be communicated with the air/water feeding nozzle 5n.

The suction pipe sleeve 2d is communicated with a suction cylinder 4s provided in the operation portion 4, through the suction pipe 3s. The suction cylinder 4s is communicated with a distal end opening 5p provided at the distal end portion of the insertion portion 5, through the suction pipe 5s.

In the vicinity of the operation portion 4, a pipe sleeve Ce of a treatment instrument insertion pipe 5t is provided. The treatment instrument insertion pipe 5t is connected with the suction pipe 5s to be communicated with the distal end opening 5p.

The air/water feeding cylinder 4aw is configured such that an air/water feeding button, not illustrated, can be set. Depending on the depressed position of the air/water feeding button, the air/water feeding cylinder 4aw opens or closes communication of the air feeding pipes 3a, 5a, or opens or closes the communication of the water feeding pipes 3w, 5w. The air/water feeding cylinder 4aw is provided with a pipe sleeve Caw.

The suction cylinder 4s is configured such that a suction button, not illustrated, can be set. Depending on the depressed position of the suction button, the suction cylinder 4s opens or closes communication of the suction pipes 3s, 5s. The suction cylinder 4s is provided with a pipe sleeve Cs.

Note that the endoscope 1 is provided with a bending portion, not illustrated, at the distal end portion of the insertion portion 5, and a bending knob for performing bending operation of the bending portion, a release button for performing photographing, and the like are provided on the operation portion 4. However, these elements are not illustrated and also the descriptions thereof will be omitted here.

Configuration of Endoscope Reprocessor 6

Figure 2:
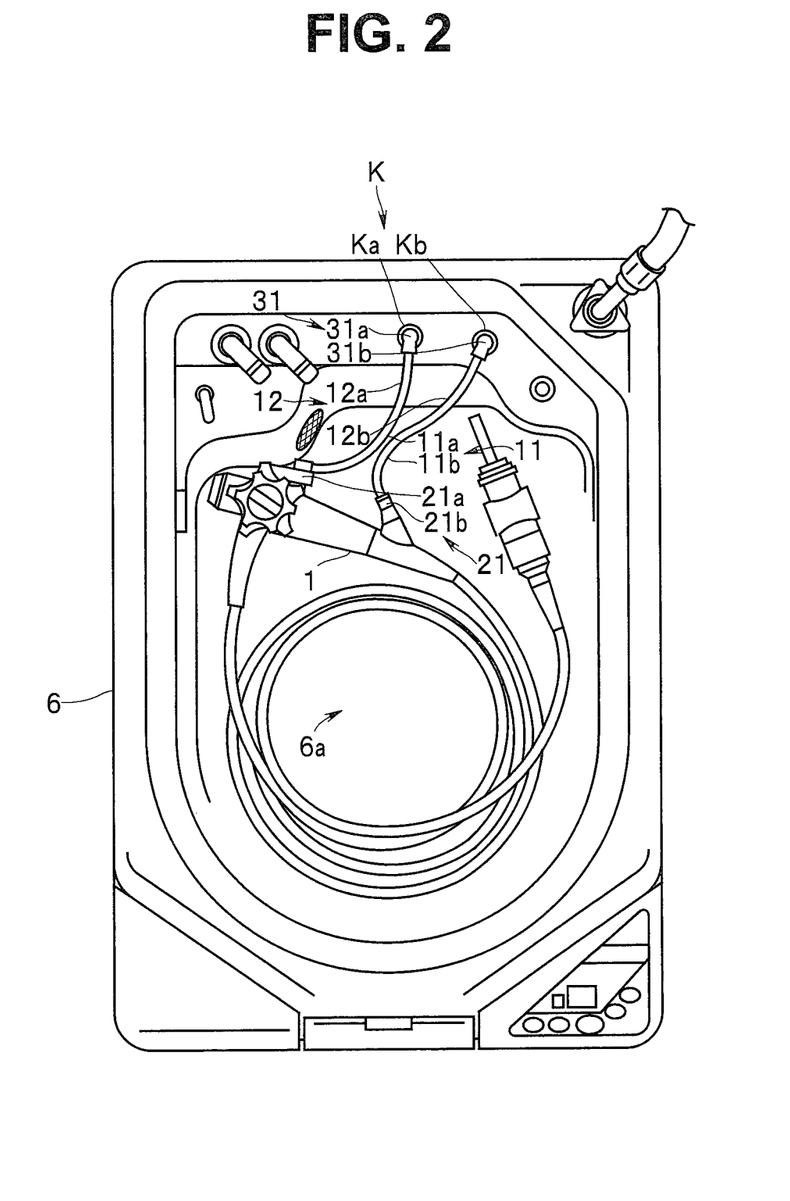
FIG. 2 illustrates one example of a processing tank of an endoscope reprocessor, the endoscope, and the endoscope connecting tube, according to the first embodiment of the present invention.
Figure 3:
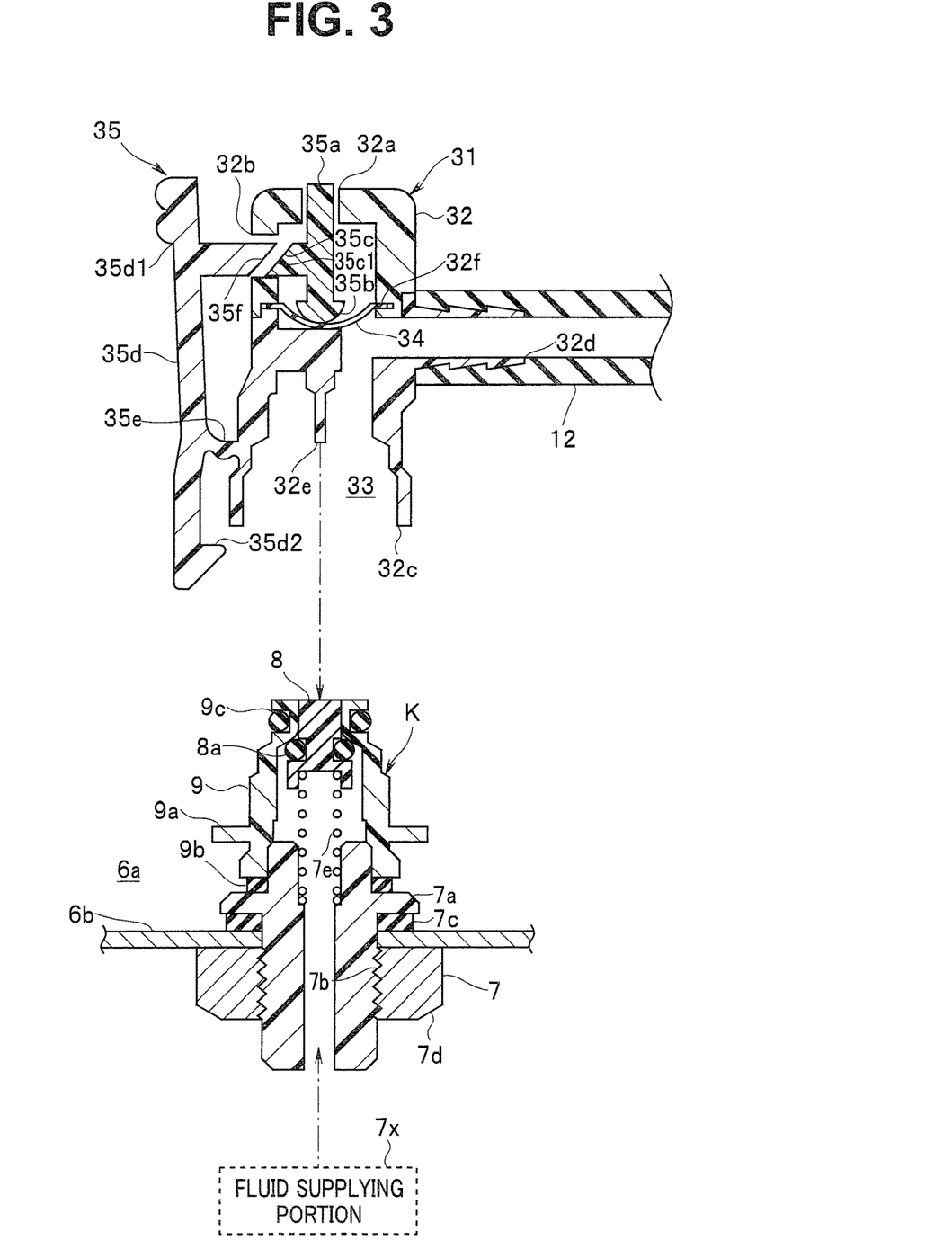
FIG. 3 is an illustration diagram of an internal configuration example of a second connection portion of the endoscope connecting tube according to the first embodiment of the present invention.

FIG. 2 illustrates one example of a processing tank 6a of the endoscope reprocessor 6, the endoscope 1, and the endoscope connecting tubes 11a and 11b according to the first embodiment of the present invention. FIG. 3 is an illustration diagram of an internal configuration example of a second connection portion 31 of the endoscope connecting tubes 11a and 11b according to the first embodiment of the present invention. FIG. 3 illustrates the cut surface cut in the axis direction of an exterior 32.

The endoscope reprocessor 6 is an apparatus for performing reprocessing of the contaminated endoscope 1, and the parts or accessories of the endoscope 1. The reprocessing referred to here is not especially limited. The reprocessing may be rinsing with water, cleaning for removing dirt such as organic substances, disinfecting for excluding predetermined microorganisms, or sterilizing for eliminating or annihilating all the microorganisms, or a combination of any of these processings. The accessories of the endoscope are not especially limited. For example, the accessories include a suction button, the air/water feeding button, the distal end cover covering the distal end portion of the endoscope, and the like. Such buttons and the distal end cover are attached to the endoscope 1 when the endoscope is used, and detached from the endoscope 1 when reprocessing of the endoscope is performed.

The endoscope reprocessor 6 includes the processing tank 6a in which the endoscope 1 is to be placed. The processing tank 6a is provided with processing tank connectors Ka, Kb.

The processing tank connectors Ka, Kb are connected to the endoscope 1 through the endoscope connecting tubes 11a and 11b, and fluid is supplied to the conduits of the endoscope 1.

That is, the endoscope reprocessor 6 is a liquid feeding apparatus for feeding liquid to the endoscope 1. However, the liquid feeding apparatus of the present invention is not limited to the endoscope reprocessor, but may be a pump, or a faucet, for example.

In the example in FIG. 2, two endoscope connecting tubes 11 are used. The one endoscope connecting tube 11a connects the processing tank connector Ka and the pipe sleeve Caw, and the other endoscope connecting tube 11b connects the processing tank connector Kb and the pipe sleeve Ce. Note that the endoscope reprocessor 6 may further include a processing tank connector Kn and may be connected to a plurality of endoscopes, though illustration of such a configuration is omitted. Hereinafter, when indicating any one of or all of the processing tank connectors Ka, Kb, and Kn, the processing connector is referred to as the processing connector K, and when indicating one of or both of the endoscope connecting tubes 11a, 11b, the endoscope connecting tube is referred to as the endoscope connecting tubes 11a and 11b.

As shown in FIG. 3, the processing tank connector K is provided on a wall plate 6b of the processing tank 6a. The processing tank connector K includes a base portion 7, a valve 8, and a body 9.

The base portion 7 is formed in a cylindrical shape, and attached to the wall plate 6b. The base portion 7 includes, on the outer circumferential portion thereof, a pressing portion 7a formed in a flange shape, and a screw portion 7b. The base portion 7 is inserted through the wall plate 6b such that the pressing portion 7a is arranged in the processing tank 6a and the screw portion 7b is arranged in the apparatus body of the endoscope reprocessor 6. A packing 7c is arranged between the pressing portion 7a and the wall plate 6b. The screw portion 7b is fastened to the wall plate 6b by a nut 7d. The proximal end of a compression spring 7e is attached to the inner circumferential portion of the base portion 7. The base portion 7 is connected with a fluid supplying portion 7x, which is a fluid supplying apparatus illustrated with the dashed lines in the drawing, of the endoscope reprocessor 6.

The valve 8 is attached to the distal end of the compression spring 7e. The valve 8 is formed in a columnar shape and biased in a direction in which the valve 8 is pushed out by the compression spring 7e. The valve 8 includes, on the outer circumferential portion thereof, an O-ring 8a pressed against the inner circumferential portion of the body 9.

The body 9 is formed in a cylindrical shape and fitted externally on the base portion 7. When the body 9 is fitted externally on the base portion 7, the body 9 communicates with the base portion 7. The body 9 includes, on the outer circumferential portion thereof, a hanging portion 9a formed in a flange shape. A packing 9b is provided at the proximal end of the body 9. An O-ring 9c is provided on the outer circumferential portion of the distal end portion of the body 9.

The endoscope reprocessor 6 includes the components for reprocessing the endoscope 1, as disclosed in the Japanese Utility Model Registration No. 3205321, for example, in addition to the processing tank connector K. However, the components are not illustrated and description thereof are also omitted here.

Configuration of Endoscope Connecting Tubes 11a and 11b

The endoscope connecting tube includes a liquid feeding index having a marker. The marker is brought into a projected state when liquid flows in the tube, and into a non-projected state when being pushed. The marker is reversibly switchable between the projected state and the non-projected state. When attaching the endoscope connecting tube to the endoscope, the user enables the marker to be in the non-projected state by grasping the endoscope connecting tube. Description will be made on the configuration of the endoscope connecting tubes 11a and 11b with reference to the drawings.

The endoscope connecting tubes 11a and 11b are configured to connect the endoscope 1 and the endoscope reprocessor 6, to enable fluid to be supplied from the endoscope reprocessor 6 to the endoscope 1. The endoscope connecting tubes 11a and 11b include a tube 12, a first connection portion 21 which is a first connector, and the second connection portion 31 which is a second connector (see FIG. 2). More specifically, the endoscope connecting tube 11a includes a tube 12a, a first connection portion 21a, and a second connection portion 31a. In addition, the endoscope connecting tube 11b includes a tube 12b, a first connection portion 21b, and a second connection portion 31b. Hereinafter, when indicating one or both of the tubes 12a, 12b, the tube is referred to as the tube 12. When indicating one or both of the first connection portions 21a, 21b, the first connection portion is referred to as the first connection portion 21. When indicating one or both of the second connection portions 31a, 31b, the second connection portion is referred to as the second connection portion 31.

The material of the tube 12 is resin or rubber, for example, and the tube 12 is formed in an elongated shape.

The first connection portion 21a is connected with the pipe sleeve Caw. The first connection portion 21b is connected with the pipe sleeve Ce. That is, the first connection portion 21 is provided at the first end portion of the tube 12 and connected to the endoscope pipe sleeve.

The second connection portion 31a is connected with the processing tank connector Ka. The second connection portion 31b is connected with the processing tank connector Kb. That is, the second connection portion 31 is provided at the second end portion of the tube 12, and connected with the processing tank connector K of the endoscope reprocessor 6. The second connection portion 31 includes the exterior 32, a flow path 33, a movable portion 34, and a liquid feeding index 35. That is, the second connection portion 31 is provided at the second end portion of the tube 12, and connected with the liquid feeding apparatus.

The exterior 32 is formed in a cylindrical shape having an upper surface so as to be finable externally on the processing tank connector K. The exterior 32 is made of resin, for example. The exterior 32 includes an exposure hole 32a, an insertion path 32b, an attaching port 32c, a discharge port 32d, a pushing rod 32e, and a holding portion 32f.

The exposure hole 32a is provided at the distal end portion of the exterior 32 and formed so as to allow the liquid feeding index 35 to be exposed.

The insertion path 32b is provided on the outer circumferential portion of the exterior 32 so as to be located on the distal end side of the exterior 32, and a releasing portion 35f of the liquid feeding index 35 is inserted into the insertion path 32b from outside of the exterior 32.

The attaching port 32c is provided at the proximal end portion of the exterior 32 such that the exterior 32 can be fitted externally to the processing tank connector K and attached thereto.

The discharge port 32d is provided on the outer circumferential portion of the exterior 32 and fitted into the tube 12. The discharge port 32d includes, on the outer circumferential portion thereof, an anti-slipping protrusion for preventing the tube 12 from falling off.

The pushing rod 32e is provided in the exterior 32 so as to enable the valve 8 to be pushed into the processing tank connector K. The pushing rod 32e is formed so as to protrude from the deep side toward the attaching port 32c.

The holding portion 32f is configured to be capable of holding the movable portion 34. The holding portion 32f is formed in a groove shape so as to enclose the inner circumferential portion of the exterior 32.

The flow path 33 is arranged in the exterior 32, to enable the attaching port 32c and the discharge port 32d to communicate with each other. That is, the flow path 33 is arranged in the exterior 32, to communicate with the tube 12.

The movable portion 34 as a movable member is made of a deformable member such as rubber, elastomer, or the like. The movable portion 34 is a board formed so as to have a round surface shape, for example. More specifically, the movable portion 34 is a membrane formed in a curved surface shape by cutting a part of a spherical body with a plane. The movable portion 34 includes a first surface formed in a convex shape and a second surface formed in a concave shape.

That is, the movable portion 34 is a board having flexibility.

The movable portion 34 includes a peripheral edge held by the holding portion 32f.

The movable portion 34 is arranged such that the first surface faces the flow path 33 and the second surface faces the liquid feeding index 35. When the first surface is pushed in by the pressure of a fluid, the movable portion 34 deforms such that the first surface becomes a concave shape and the second surface becomes a convex shape, and the deformed state is maintained. When the second surface is pushed in by the liquid feeding index 35 in the deformed state, the movable portion 34 is restored such that the shape in which the first surface is convex and the second surface is concave.

That is, the movable portion 34 is arranged in the exterior 32. The movable portion 34 is brought into a convex warp state toward the surface direction of the exterior 32 when the inner pressure of the flow path 33 reaches a predetermined value or higher, and the movable portion 34 remains in the convex warp state even when the inner pressure of the flow path 33 reaches less than the predetermined value.

The liquid feeding index 35 is configured to be capable of indicating to the user whether or not the liquid has been fed. The liquid feeding index 35 is made of resin or metal, for example. The liquid feeding index 35 includes a marker 35a, a contact portion 35b, a receiving portion 35c, a fixing portion 35d, a supporting portion 35e, and a releasing portion 35f.

The marker 35a is configured to be visually recognizable by the user. The marker is brought into a pushed-in state before the liquid is fed, and brought into a projected state by feeding the liquid. The marker 35a is formed in a columnar shape, for example, and inserted into the exposure hole 32a.

That is, the marker 35a is arranged so as to contact the movable portion 34, and projected from the exposure hole 32a by the movable portion 34 being brought into the convex warp state.

The contact portion 35b is provided at the proximal end of the marker 35a so as to contact the movable portion 34. The contact portion 35b is formed in a round surface shape.

The receiving portion 35c is formed so as to protrude from the outer circumferential portion of the marker 35a toward the insertion path 32b. The receiving portion 35c includes a tapered portion 35c1 that is inclined in the direction of the contact portion 35b as going toward the insertion path 32b.

That is, the marker 35a is arranged such that the proximal end contacts the movable portion 34, and the marker 35a includes the tapered portion 35c1 which is formed so as to protrude from the outer circumferential portion of the marker 35a toward the insertion path 32b and so as to be inclined in the direction of the proximal end as going toward the insertion path 32b.

The fixing portion 35d is capable of fixing the second connection portion 31 to the processing tank connector K. The fixing portion 35d includes a knob 35d1 and a hook 35d2. The knob 35d1 is arranged on the distal end side of fixing portion 35d so that the user can easily pinch with his or her fingers. The hook 35d2 is arranged on the proximal end side of fixing portion 35d so as to be hookable on the hanging portion 9a. That is, the fixing portion 35d includes the knob 35d1 located on one end of the fixing portion so as to be opposed to the insertion path 32b and the hook 35d2 arranged at the other end of the fixing portion.

The supporting portion 35e is provided so as to protrude from the outer circumferential portion of the exterior 32. The supporting portion 35e supports the part between the knob 35d1 and the hook 35d2 of the fixing portion 35d. The supporting portion 35e is arranged between the knob 35d1 and the hook 35d2, to thereby connect the fixing portion 35d to the exterior 32 such that the hook 35d2 gets away from the exterior 32 when the knob 35d1 is pressed against the exterior 32.

The releasing portion 35f is configured to be capable of releasing the projected state in which the marker 35a is projected from the exposure hole 32a. The releasing portion 35f is formed so as to protrude from the knob 35d1 toward the insertion path 32b, and inserted into the insertion path 32b by the knob 35b1 being pressed. The releasing portion 35f may have a distal end portion formed in a tapered shape along the receiving portion 35c.

That is, the releasing portion 35f is provided so as to protrude from the knob 35d1. The releasing portion 35f enters from the insertion path 32b into the inside of the exterior 32 by the knob 35d1 being pressed against the exterior 32, and releases the convex warp state of the movable portion 34 by causing the marker 35a to slide toward the movable portion 34 to push the movable portion 34.

Working of the Endoscope Connecting Tubes 11a and 11b

Next, description will be made on the working of the endoscope connecting tubes 11a and 11b according to the present embodiment.

Figure 4:
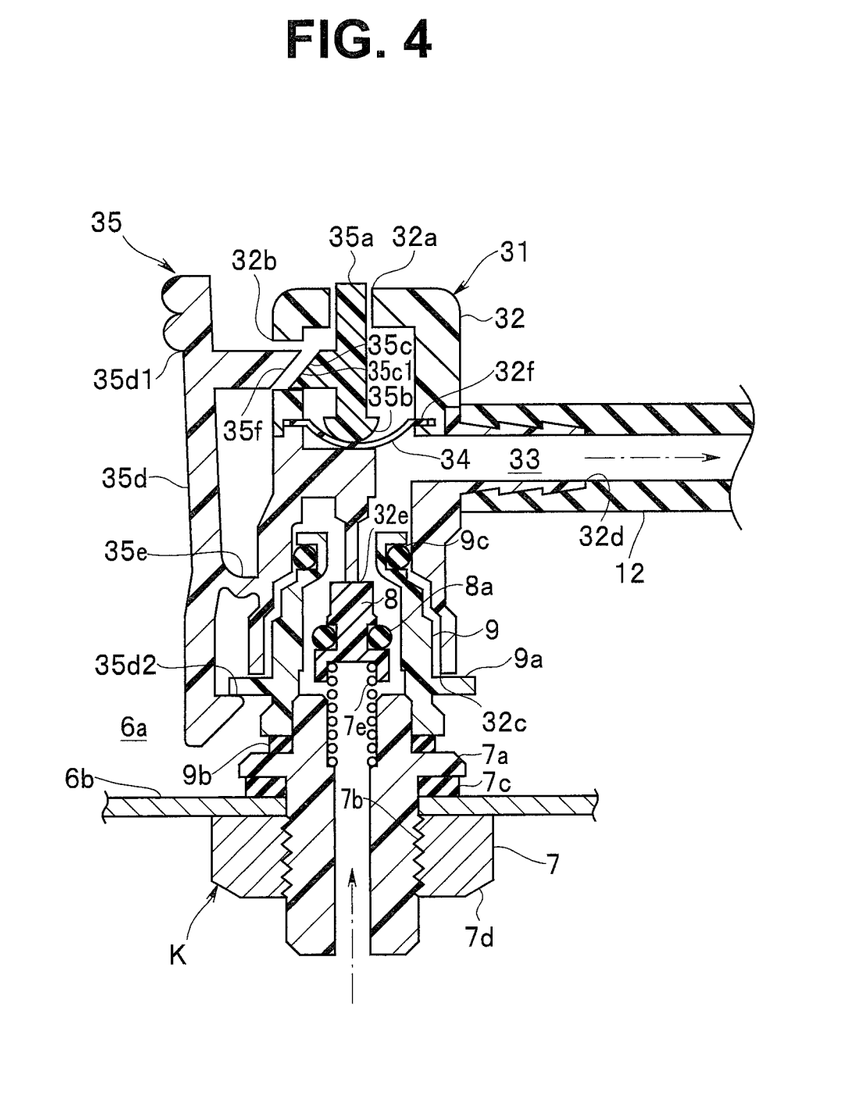
FIG. 4 is an illustration diagram of the internal configuration example of the second connection portion of the endoscope connecting tube according to the first embodiment of the present invention.
Figure 5:
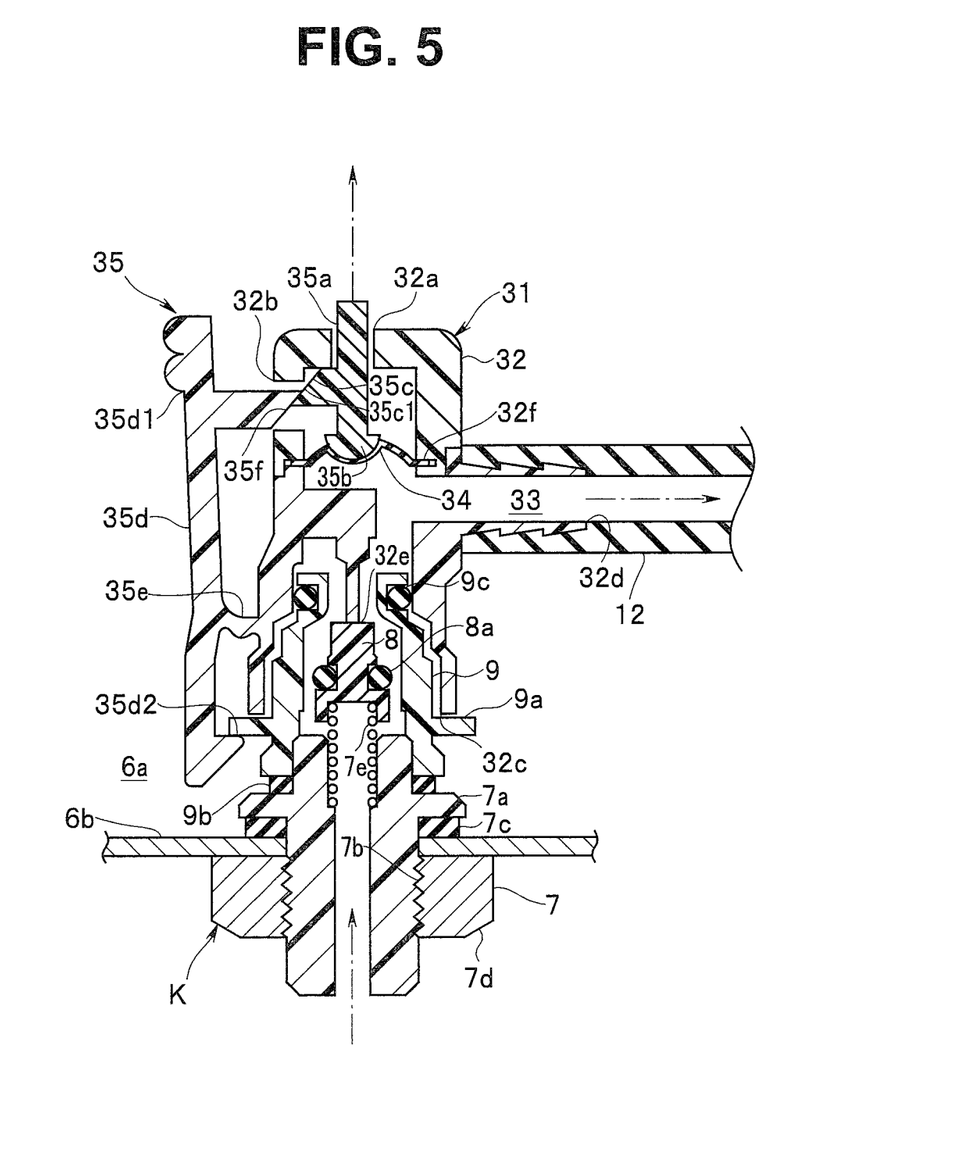
FIG. 5 is an illustration diagram of the internal configuration example of the second connection portion of the endoscope connecting tube according to the first embodiment of the present invention.
Figure 6:
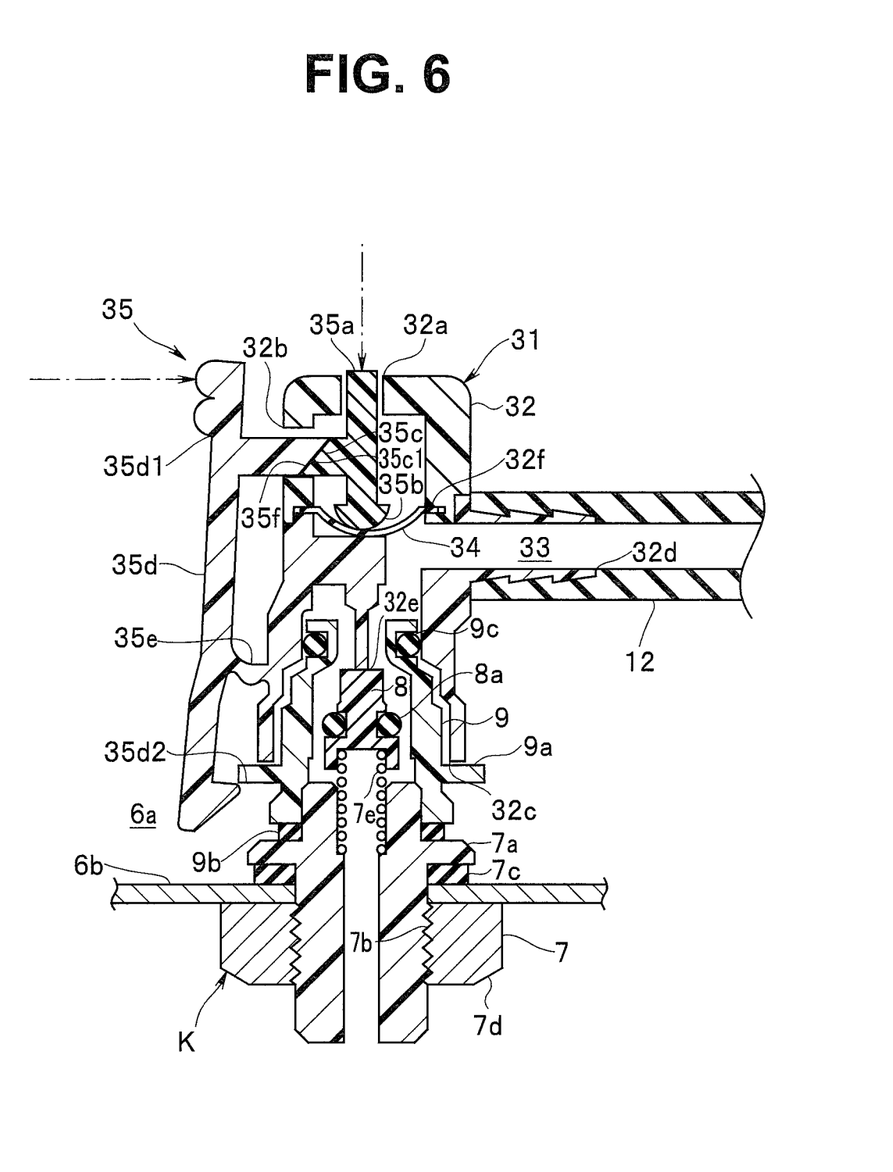
FIG. 6 is an illustration diagram of the internal configuration example of the second connection portion of the endoscope connecting tube according to the first embodiment of the present invention.

FIGS. 4 to 6 are illustration diagrams each illustrating the internal configuration example of the second connection portion 31 of the endoscope connecting tubes 11a and 11b according to the first embodiment of the present invention. FIGS. 4 to 6 illustrate the cut surface cut in the axis direction of the exterior 32.

When the user places his or her fingers on the distal end of the marker 35a to push in the marker 35a, and fits the second connection portion 31 externally on the processing tank connector K, the marker 35a is brought into a pushed-in state. In addition, the movable portion 34 is brought into a state where the first surface is convex and the second surface is concave by the contact portion 35b. Note that the marker 35a may be brought into the pushed-in state by the user pinching the knob 35d1 with his or her fingers to insert the releasing portion 35f into the insertion path 32b.

As shown in FIG. 4, when the second connection portion 31 is fitted externally on the processing tank connector K, the pushing rod 32e pushes the valve 8 against the compression spring 7e, and the O-ring 9c contacts the inner circumferential portion of the second connection portion 31, which allows the inside of the processing tank connector K and the flow path 33 to communicate with each other in a water-tight manner. When the hook 35d2 is hooked on the hanging portion 9a, the second connection portion 31 is fixed to the processing tank connector K.

As shown in FIG. 5, when a fluid supplying portion of the endoscope reprocessor 6 is driven, fluid is supplied from the processing tank connector K to the tube 12 through the flow path 33.

The fluid supplied to the pipe sleeves Caw and Ce through the endoscope connecting tubes 11a and 11b pass through the air feeding pipe 3a, the water feeding pipe 3w, the air feeding pipe 5a, the water feeding pipe 5w, the treatment instrument insertion pipe 5t, the suction pipe 5s, and the suction pipe 3s, to be discharged into the processing tank 6a.

When the inner pressure of the flow path 33 reaches a predetermined value or higher, the movable portion 34 is brought into a deformed state in which the first surface is concave and the second surface is convex by the force received from the fluid. Then, the movable portion 34 pushes the contact portion 35b, to thereby bring the marker 35a into the projected state. Even if the inner pressure of the flow path 33 reaches less than the predetermined value, the deformed state of the movable portion 34 and the projected state of the marker 35a are maintained.

As shown in FIG. 6, when the user presses the knob 35d1 against the exterior 32 with his or her fingers, the hook 35d2 comes off from the hanging portion 9a, and the releasing portion 35f is inserted into the insertion path 32b. The releasing portion 35f contacts the tapered portion 35c1, to cause the marker 35a to slide toward the movable portion 34. Then, the marker 35a is brought into the pushed-in state by the releasing portion 35f. When the contact portion 35b contacts the movable portion 34 by the movement of the marker 35a, the first surface, which is located on the side of the flow path 33, of the movable portion 34 becomes a convex shape.

With such a configuration, even after the power source of the endoscope reprocessor 6 has been turned off, the projected state of the marker 35a, which indicates that the reprocessing has been completed, is maintained, and the marker 35a is brought into the pushed-in state which surely indicates that the endoscope is not cleaned, when the endoscope connecting tube is attached or detached.

According to the above-described embodiment, the endoscope connecting tubes 11a and 11b are capable of indicating whether the endoscope 1 has been reprocessed or not by the marker 35a without relying on electric power.

Second Embodiment

In the first embodiment, the liquid feeding index 35 is provided to the second connection portion 31. However, a liquid feeding index 45 may be provided to a first connection portion 41.

Figure 7:
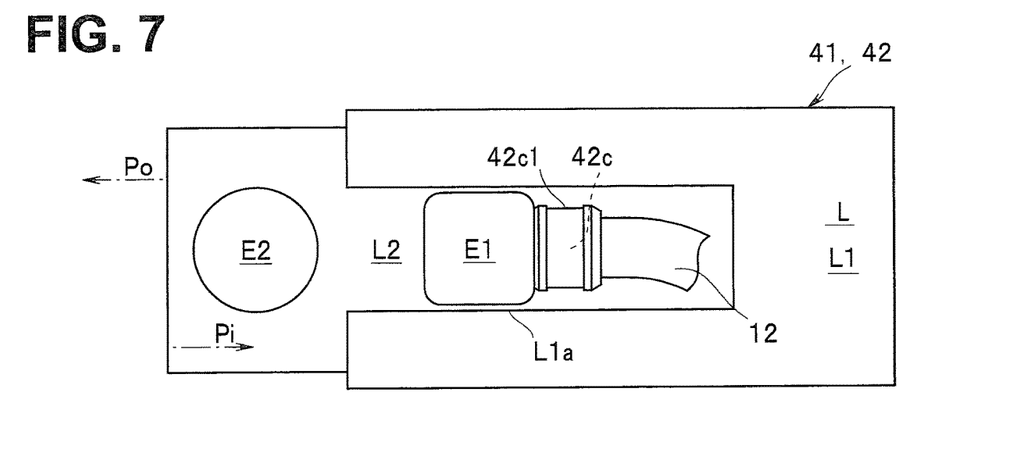
FIG. 7 is a plan view illustrating one example of a first connection portion of an endoscope connecting tube according to a second embodiment of the present invention.
Figure 8:
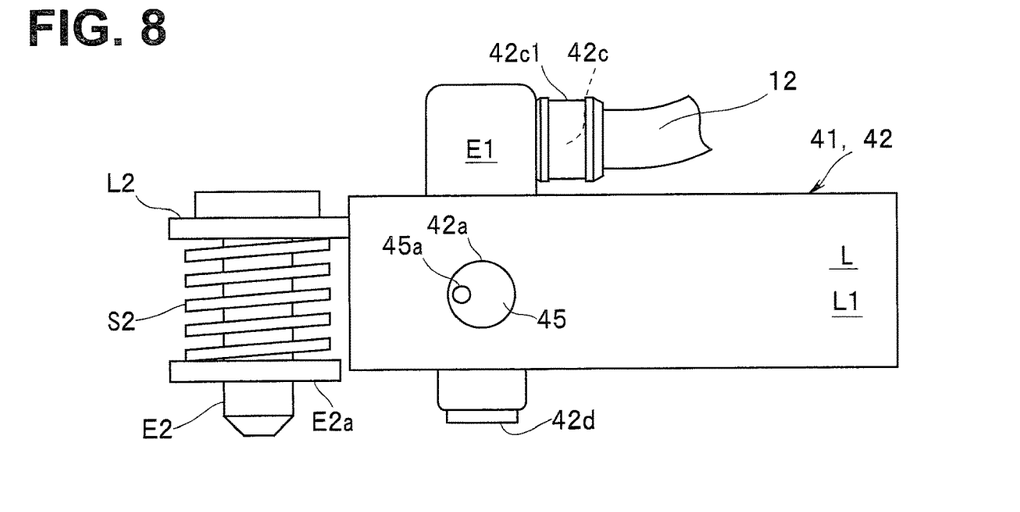
FIG. 8 is a side view illustrating one example of the first connection portion of the endoscope connecting tube according to the second embodiment of the present invention.
Figure 9:
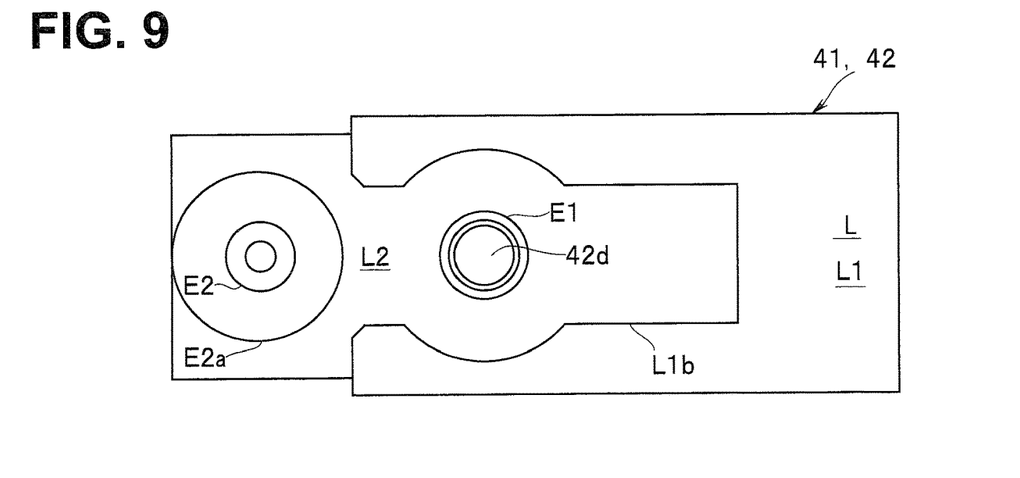
FIG. 9 is a bottom view illustrating one example of the first connection portion of the endoscope connecting tube according to the second embodiment of the present invention.
Figure 10:
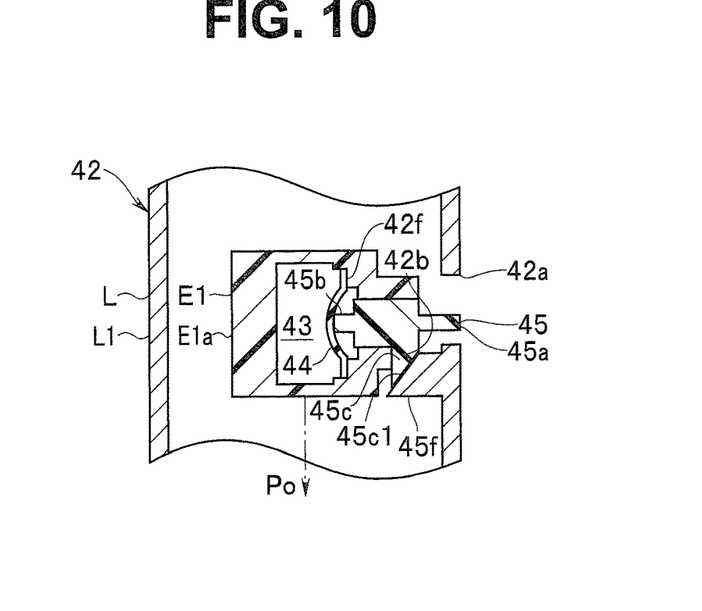
FIG. 10 is an illustration diagram of an internal configuration example of the first connection portion of the endoscope connecting tube according to the second embodiment of the present invention.
Figure 11:
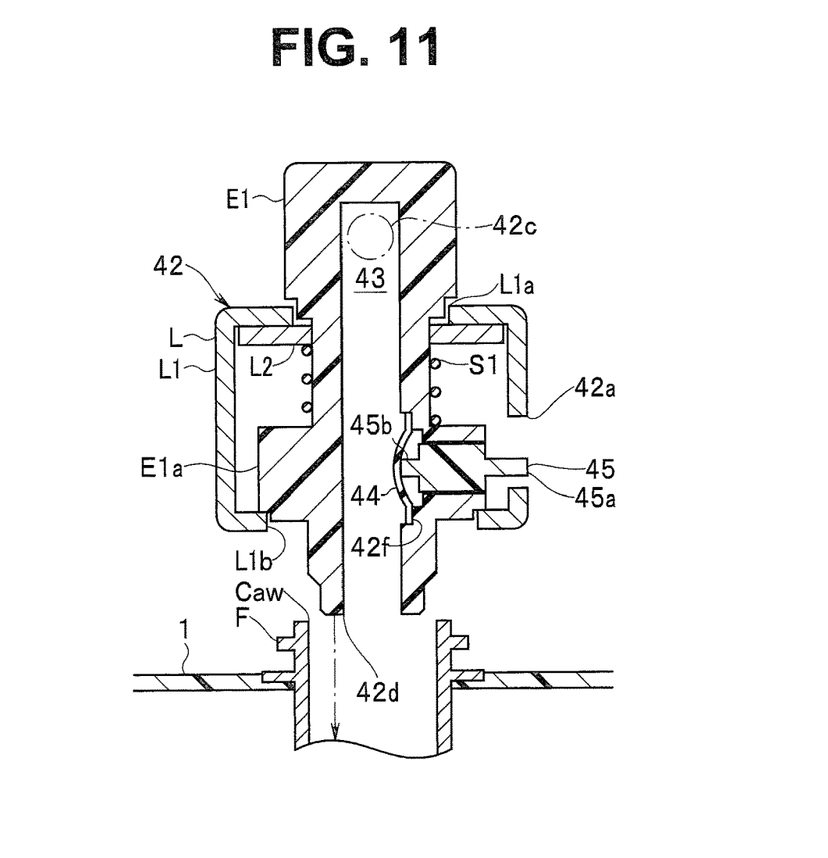
FIG. 11 is an illustration diagram of the internal configuration example of the first connection portion of the endoscope connecting tube according to the second embodiment of the present invention.

FIGS. 7 to 9 illustrate one example of the first connection portion 41 of the endoscope connecting tubes 11a and 11b according to the second embodiment of the present invention. FIG. 7 is a plan view, FIG. 8 is a side view, and FIG. 9 is a bottom view. FIGS. 10 and 11 are illustration diagrams of the internal configuration example of the first connection portion 41 of the endoscope connecting tubes 11a and 11b according to the second embodiment of the present invention. FIG. 10 illustrates the end surface of the cut portion cut in a direction orthogonal to the axis direction of an exterior body E1. FIG. 11 illustrates the end surface of the cut portion cut in the axis direction of the exterior body E1 and the pipe sleeve Caw. In the description of the present embodiment, descriptions of the same configurations as those in the first embodiment will be omitted.

The endoscope connecting tubes 11a and 11b include the first connection portion 41.

The first connection portion 41 is provided at a first end portion which is one end portion of the tube 12, and connected with the pipe sleeve Caw. The first connection portion 41 includes an exterior 42, a flow path 43, a movable portion 44, and a liquid feeding index 45.

As shown in FIGS. 7 to 9, the exterior 42 includes the exterior body E1 and a slide lock L.

As shown in FIGS. 10 and 11, the exterior body E1 is made of resin or metal material and formed in a cylindrical shape, and includes a base E1a formed by extending a part of the outer circumference of the exterior body.

The slide lock L is made of resin or metal material, for example, and configured so as to allow the exterior body E1 to be attached to the pipe sleeve Caw. The slide lock L includes a case L1 and a slide plate L2.

The case L1 is formed in a square cylinder shape. The case L1 includes guide grooves L1a and L1b formed so as to be opposed to each other.

The slide plate L2 is formed in a plate shape and attached to the outer circumferential portion of the exterior body E1. The slide plate L2 is slidably inserted in the case L1. A compression spring S1 is provided between the slide plate L2 and the base E1a. The base E1a is biased by the compression spring S1 in a direction away from the slide plate L2.

The slide plate L2 is not only configured to be attachable to the exterior body E1, but includes a columnar body E2 to be attached to the pipe sleeve Cs. The columnar body includes, on the outer circumferential portion thereof, a plate member E2a which is biased by a compression spring S2 in the direction away from the slide plate L2.

The exterior 42 includes an exposure hole 42a, an insertion path 42b, an attaching port 42c, a discharge port 42d, and a holding portion 42f, in addition to the exterior body E1 and the slide lock L.

The exposure hole 42a is provided on the wall portion of the slide lock L, and formed so as to allow the liquid feeding index 45 to be exposed.

The insertion path 42b is provided on the outer circumferential portion of the base E1a, and a releasing portion 45f is inserted into the insertion path 42b from outside of the exterior body E1.

The attaching port 42c is provided in the direction intersecting the exterior body E1, with the exterior body E1 bent in an L shape. The attaching port 42c includes, on the outer circumferential portion thereof, an anti-slipping protrusion, not illustrated. The attaching port 42c is fitted in the tube 12. As shown in FIGS. 7 and 8, after the attaching port 42c is fitted in the tube 12, a tube stopper 42c1 formed in a ring shape is fitted externally on the tube 12, as a retainer of the tube 12.

The discharge port 42d is formed in a cylindrical shape so as to be fitted in the pipe sleeve Caw.

The holding portion 42f is configured to be capable of holding the movable portion 44. The holding portion 42f is formed in a concave shape around the through hole formed on the peripheral wall of the inner circumferential portion of the exterior body E1.

The flow path 43 is arranged inside the exterior body E1, to allow the attaching port 42c and the discharge port 42d to communicate with each other. That is, the flow path 43 is arranged in the exterior 42 to be communicated with the tube 12.

The movable portion 44 has a peripheral edge portion held by the holding portion 42f. More specifically, the movable portion 44 is attached to the holding portion 42f with adhesive. Note that the movable portion 44 is attached to the holding portion 42f with adhesive in the present embodiment, but the movable portion 44 may be attached by using a method other than the adhesive. For example, the movable portion 44 may be held by a fitting member fitted in the holding portion 42f, or may be held by a screw member screwed in the holding portion 42f.

The liquid feeding index 45 is configured to be capable of indicating to the user whether the liquid has been fed. The liquid feeding index 45 includes a marker 45a, a contact portion 45b, a receiving portion 45c, and a releasing portion 45f.

The marker 45a is formed in a columnar shape, for example, inserted in the exposure hole 42a, and arranged so as to contact the movable portion 44. That is, the marker 45a is arranged so as to contact the movable portion 44, and exposed from the exposure hole 42a by movable portion 44 being brought into the convex warp state.

The contact portion 45b is configured so as to contact the movable portion 44. The contact portion 45b is provided on the proximal end of the marker 45a.

The receiving portion 45c is provided at the position contacting the releasing portion 45f when the slide plate L2 is pulled out. The receiving portion 45c is formed so as to protrude from the outer circumferential portion of the marker 45a toward the insertion path 42b. The receiving portion 45c includes a tapered portion 45c1 inclined in the direction of the contact portion 45b as going toward the insertion path 42b. That is, the marker 45a is arranged such that the proximal end contacts the movable portion 44, and the marker 45a includes the tapered portion 45c1 which is formed so as to protrude from the outer circumferential portion of the marker 45a toward the insertion path 42b and so as to be inclined in the direction of the proximal end as going toward the insertion path 42b.

The releasing portion 45f is configured to be capable of releasing the projected state where the marker 45a is projected from the exposure hole 42a. The releasing portion 45f protrudes from the inside of the case L1 toward the insertion path 42b, and is formed to be insertable into the insertion path 42b by the sliding of the slide plate L2.

Description will be made on the working of the endoscope connecting tubes 11a and 11b according to the present embodiment.

Figure 12:
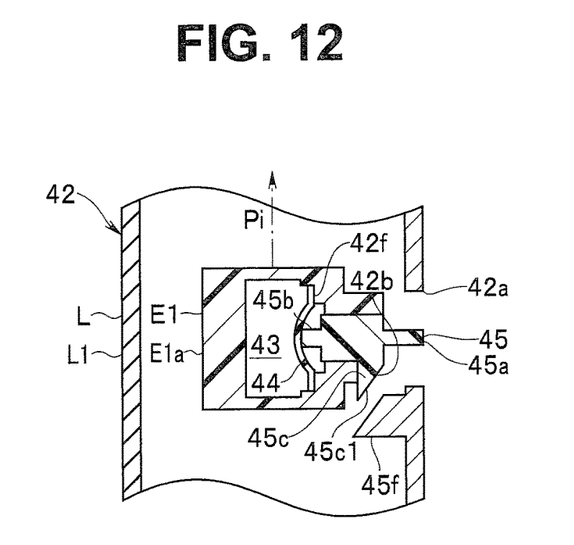
FIG. 12 is an illustration diagram of the internal configuration example of the first connection portion of the endoscope connecting tube according to the second embodiment of the present invention.
Figure 13:
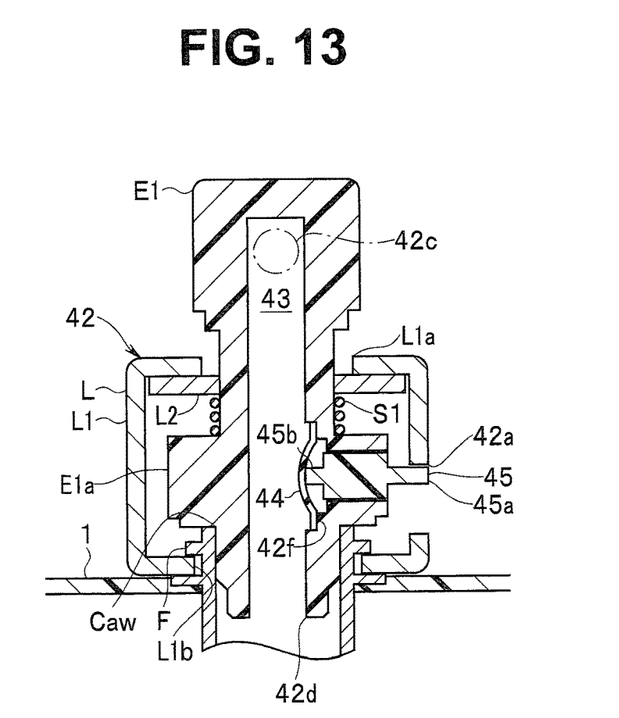
FIG. 13 is an illustration diagram of the internal configuration example of the first connection portion of the endoscope connecting tube according to the second embodiment of the present invention.
Figure 14:
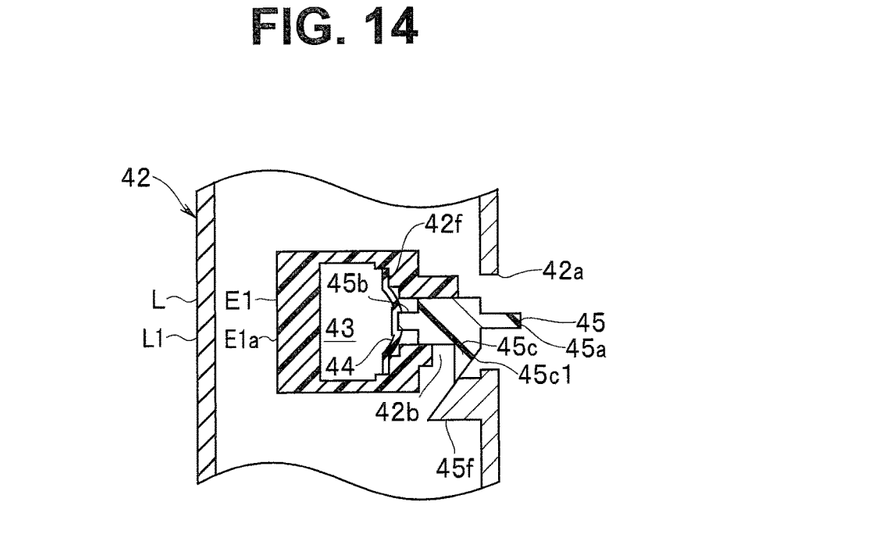
FIG. 14 is an illustration diagram of the internal configuration example of the first connection portion of the endoscope connecting tube according to the second embodiment of the present invention.
Figure 15:
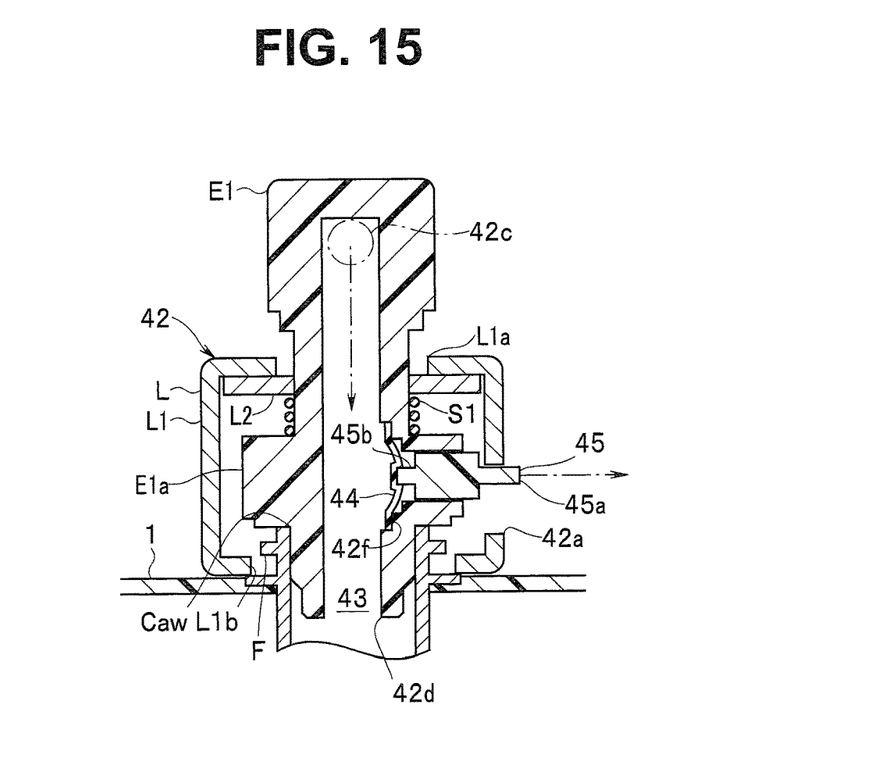
FIG. 15 is an illustration diagram of the internal configuration example of the first connection portion of the endoscope connecting tube according to the second embodiment of the present invention.

FIGS. 12 to 15 are illustration diagrams each illustrating the internal configuration example of the first connection portion 41 of the endoscope connecting tubes 11a and 11b according to the second embodiment of the present invention. FIGS. 12 and 14 illustrate the cut surface cut in the direction orthogonal to the axis direction of the exterior body E1. FIGS. 13 and 15 illustrate the cut surface cut in the axis direction of the exterior body E1 and the pipe sleeve Caw.

When the user pulls out the slide plate L2, the insertion path 42b moves together with the exterior body E1 in the pulling direction Po, the releasing portion 45f contacts the tapered portion 45c1, the marker 45a slides toward the movable portion 44, and the marker 45a is brought into the pushed-in state (FIG. 10). Furthermore, the contact portion 45b is pushed to contact the movable portion 44, and the first surface, which is located on the side of the flow path 43, of the movable portion 44 becomes the convex shape (FIG. 11). When the slide plate L2 is pulled out, the discharge port 42d comes out of the case L1.

Next, the user inserts the discharge port 42d into the pipe sleeve Caw, inserts the columnar body E2 into the pipe sleeve Cs, and pushes the case L1 against the endoscope 1 such that the flange F of the pipe sleeve Caw enters the case L1 against the compression springs S1, S2. Next, when the user causes the case L1 to slide so as to accommodate the slide plate L2, the exterior body E1 moves toward the accommodating direction Pi (FIG. 12). Then, the base E1a moves in the direction in which the base E1a is accommodated in the case L1 such that the edge portion of the guide groove L1b and the flange F overlap with each other. As a result, the case L1 is engaged with the flange F, to thereby cause the exterior 42 to be attached to the pipe sleeve Caw (FIG. 13).

Note that the user may attach the exterior 42 to the pipe sleeve Caw by placing his or her fingers on the distal end of the marker 45a to push in the marker 45a and grasping the case L1 with the fingers.

When the fluid supplying portion of the endoscope reprocessor 6 is driven, fluid is supplied from the tube 12 into the pipe sleeve Caw through the flow path 43. When the inner pressure of the flow path 43 reaches a predetermined value or higher, the movable portion 44 is brought into the deformed state in which the first surface is concave and the second surface is convex by the force received from the fluid, which brings the marker 45a into the projected state (FIGS. 14, 15).

When the user pulls out the slide plate L2 in the pulling direction Po after the reprocessing is terminated, the releasing portion 45f causes the marker 45a to slide toward the movable portion 44, to bring the marker 45a into the pushed-in state (FIG. 10).

That is, the releasing portion 45f is provided in a protruded manner inside the case L1, and enters the insertion path 42b by the slide plate L2 being pulled out. The releasing portion 45f causes the marker 45a to slide toward the movable portion 44 to push the movable portion 44, to thereby release the convex warp state of the movable portion 44.

The second connection portion 31 is provided at the second end portion which is one end portion of the tube 12, and connected with the processing tank connector K. The second connection portion 31 according to the present embodiment does not include the movable portion 34 and the marker 35a.

According to the above-described embodiment, the endoscope connecting tubes 11a and 11b are capable of indicating whether the endoscope 1 has been reprocessed or not by the marker 45a without relying on electric power.

Note that each of the liquid feeding indices 35, 45 is arranged to either one of the first connection portion or the second connection portion in the embodiments. However, the liquid feeding indices 35, 45 have only to be arranged to at least one of the first connection portion and the second connection portion. For example, the liquid feeding indices 35, 45 may be arranged respectively to both of the first connection portion and the second connection portion.

Note that the tube 12 includes the first end portion and the second end portion in the embodiments. However, the tube 12 may be branched at the halfway portion thereof and may include a third end portion connected with the first connection portion 21 or 41, or the second connection portion 31.

In the first embodiment, the example in which the one knob 35d1 is provided has been described. However, two knobs 35d1 may be provided so as to allow the user to easily hold the knobs with his or her fingers.

Note that the movable portion 34 is formed such that the peripheral edge portion is held by the groove formed on the inner circumferential portion of the exterior 32 in the first embodiment. However, the movable portion 34 may be formed such that the pressure of the fluid discharged from the discharge port 32d is adjusted and a part of the peripheral edge portion of the movable portion is held by the inner circumferential portion of the exterior. For example, the movable portion 34 may be configured by arranging a thin and long plate at the center or on the one side of the inner circumferential portion of the exterior.

The present invention is not limited to the above-described embodiments, but various changes and modifications are possible without changing the gist of the present invention.

With the present invention, it is possible to provide an endoscope connecting tube that connects an endoscope reprocessor and an endoscope and is capable of indicating whether the endoscope has been reprocessed without relying on electric power.

What is claimed is:

1. An endoscope connecting tube comprising:
   a tube;
   a first connector provided at a first end portion of the tube, and configured to be connected to an endoscope pipe sleeve;
   a second connector provided at a second end portion of the tube, and configured to be connected to a liquid feeding apparatus; and
   a liquid feeding index provided at one or more of the first connector and the second connector, the liquid feeding index comprising:
      an exterior;
      an exposure hole formed on the exterior;
      a flow path arranged in the exterior and communicated with the tube;
      a deformable material arranged in the exterior so as to be deformed from a first state when an inner pressure of the flow path is below a predetermined pressure to a second state when the inner pressure is greater than the predetermined pressure, the deformable material being configured to remain in the second state when the inner pressure of the flow path returns from above the predetermined pressure to below the predetermined pressure; and
      a marker biased by the deformable material to project from the exposure hole when the deformable material is in the second state.

2. The endoscope connecting tube according to claim 1, wherein the deformable material is a board having flexibility.

3. The endoscope connecting tube according to claim 1, wherein the exterior holds a peripheral edge of the deformable material.

4. The endoscope connecting tube according to claim 1, wherein the liquid feeding index comprises:
   a knob provided so as to be configured to move relative to the exterior; and
   a releasing portion configured to return the deformable material from the second state to the first state by causing the marker to slide toward the deformable material and push the deformable material into the first state.

5. The endoscope connecting tube according to claim 1, wherein
   the exterior includes a holding portion formed in a concave shape around a through hole formed on a part of a circumferential wall of an inner circumferential portion of the exterior, and
   the holding portion holds a peripheral edge of the deformable material.

6. The endoscope connecting tube according to claim 1, further comprising:
   a releasing portion configured to release the second state of the deformable material by causing the marker to slide and push the deformable material into the first state; and
   wherein the exterior having an insertion path, the releasing portion being configured to be inserted into the insertion path.

7. The endoscope connecting tube according to claim 6, wherein the marker is arranged such that a proximal end of the marker contacts the deformable material, and the marker includes a tapered portion protruding from an outer circumferential portion of the marker toward the insertion path, the tapered portion being inclined such that the tapered portion contacts the releasing portion when the deformable material is in the second state.

8. The endoscope connecting tube according to claim 6, wherein
   the exterior comprises a slide lock,
   the slide lock comprises a case and a slide plate slidably inserted in the case, and
   the liquid feeding index includes the releasing portion protruding from an inside of the case toward the insertion path, the releasing portion being configured to be insertable into the insertion path by the slide plate being slid.

9. The endoscope connecting tube according to claim 8, wherein the releasing portion is configured to move in response to a motion of the slide plate.

10. The endoscope connecting tube according to claim 1, wherein the deformable material is configured to seal the exposure hole from the flow path such that the deformable material is brought into the second state by the inner pressure of the flow path.

11. A liquid feeding apparatus comprising:
    a fluid supplying apparatus;
    a connector communicating with the fluid supplying apparatus; and
    an endoscope connecting tube comprising:
       a tube;
       a first connector provided at a first end portion of the tube, and configured to be connected to an endoscope pipe sleeve;
       a second connector provided at a second end portion of the tube, and configured to be connected to a liquid feeding apparatus; and
       a liquid feeding index provided at one or more of the first connector and the second connector, the liquid feeding index comprising:
          an exterior;
          an exposure hole formed on the exterior;
          a flow path arranged in the exterior and communicated with the tube;
          a deformable material arranged in the exterior so as to be deformed from a first state when an inner pressure of the flow path is below a predetermined pressure to a second state when the inner pressure is greater than the predetermined pressure, the deformable material being configured to remain in the second state when the inner pressure of the flow path returns from above the predetermined pressure to below the predetermined pressure; and
          a marker biased by the deformable material to project from the exposure hole when the deformable material is in the second state.

12. The liquid feeding apparatus according to claim 11, further comprising:
    a releasing portion configured to release the second state of the deformable material by causing the marker to slide and push the deformable material into the first state; and an insertion path into which the releasing portion is inserted, the insertion path being formed on the exterior.

13. An endoscope connecting tube comprising:
a liquid feeding index comprising a marker configured to be reversibly switchable between a projected state and a non-projected state; and
a tube,
wherein the marker is brought into the projected state and maintained in the projected state when liquid flows in the tube.

14. The endoscope connecting tube, according to claim 13, further comprising a releasing position configured to push the marker so as to bring the marker into the projected state from the non-projected state.

15. The endoscope connecting tube, according to claim 13, wherein the liquid feeding index comprises a deformable material arranged so as to be deformed from a first state when an inner pressure in the tube is below a predetermined pressure to a second state when the inner pressure in the tube is greater than the predetermined pressure, the first state of the deformable material corresponding to the non-projected state of the marker and the second state of the deformable material corresponding to the projected state of the marker.

16. The endoscope connecting tube, according to claim 15, wherein the liquid feeding index comprises an exterior holding a peripheral edge of the deformable material.

17. The endoscope connecting tube according to claim 15, further comprising,
a flow path arranged in an exterior and in fluid communication with the tube;
wherein the deformable material is configured to seal a part of the flow path such that the deformable material is brought into the second state by the inner pressure of the flow path.

18. The endoscope connecting tube according to claim 16, wherein the exterior is configured to connect to an endoscope.

19. An endoscope reprocessing method comprising,
pushing a releasing portion configured to bring a marker from a projected state into a non-projected state; and
connecting an endoscope connecting tube to an endoscope;
wherein the marker is provided on the endoscope connecting tube.

20. The endoscope reprocessing method, according to claim 19, further comprising:
injecting fluid into a conduit of the connecting tube;
switching a state of the marker from the non-projected state to the projected state by the fluid; and
maintaining the projected state after the switching.

* * * * *